(12) United States Patent
Garelick et al.

(10) Patent No.: US 7,442,177 B1
(45) Date of Patent: *Oct. 28, 2008

(54) HAND BRACE

(75) Inventors: David H. Garelick, Chicago, IL (US); Edward L. Cotton, South Holland, IL (US); James J. Weber, Santa Barbara, CA (US)

(73) Assignee: Weber Orthopedic Inc., Santa Paula, CA (US)

( * ) Notice: Subject to any disclaimer, the term of this patent is extended or adjusted under 35 U.S.C. 154(b) by 70 days.

This patent is subject to a terminal disclaimer.

(21) Appl. No.: 11/247,766

(22) Filed: Oct. 12, 2005

Related U.S. Application Data

(60) Division of application No. 11/097,701, filed on Apr. 4, 2005, now Pat. No. 7,278,980, which is a continuation-in-part of application No. 10/856,304, filed on Jun. 1, 2004, now Pat. No. 7,276,039.

(51) Int. Cl.
  *A61F 5/00* (2006.01)
  *A61F 5/37* (2006.01)
  *A41D 13/08* (2006.01)
  *A41D 10/00* (2006.01)
  *A63B 71/14* (2006.01)
  *A61F 13/00* (2006.01)

(52) U.S. Cl. .................. 602/21; 602/5; 602/6; 602/12; 602/20; 602/22; 128/879

(58) Field of Classification Search ............ 602/20–22, 602/62–64; 128/878, 880, 881, DIG. 15; 2/16, 19
See application file for complete search history.

(56) References Cited

U.S. PATENT DOCUMENTS

| | | | | | |
|---|---|---|---|---|---|
| 4,407,499 | A | * | 10/1983 | Newton | 473/61 |
| 5,058,576 | A | * | 10/1991 | Grim et al. | 602/21 |
| 5,160,314 | A | * | 11/1992 | Peters | 602/21 |
| 5,415,624 | A | * | 5/1995 | Williams | 602/21 |
| 5,728,059 | A | * | 3/1998 | Wiesemann et al. | 602/64 |
| 5,772,620 | A | * | 6/1998 | Szlema et al. | 602/21 |
| 6,102,880 | A | * | 8/2000 | Nelson et al. | 602/21 |
| 6,190,344 | B1 | * | 2/2001 | Bobroff | 602/21 |
| 6,261,253 | B1 | * | 7/2001 | Katzin | 602/21 |
| 6,561,994 | B1 | * | 5/2003 | Mills et al. | 602/20 |
| 6,730,053 | B1 | * | 5/2004 | Bodenschatz et al. | 602/64 |
| 6,913,582 | B2 | * | 7/2005 | Chen et al. | 602/5 |

* cited by examiner

*Primary Examiner*—Patricia Bianco
*Assistant Examiner*—Brandon Jackson
(74) *Attorney, Agent, or Firm*—William W. Haefliger

(57) ABSTRACT

A finger and hand brace, the combination comprising a longitudinally elongated brace body, adapted to be applied lengthwise to the wrist and finger region of the hand; multiple flexible flaps carried by the body to be spaced lengthwise thereof and to extend from the body; separate flaps configured to be wrapped about at least two of the following: hand, wrist, a finger or fingers; and retention means on the brace to retain the flaps in wrapped condition; and two generally longitudinally elongated stiffeners carried by the body, the stiffeners having undulating extent or extents, to readily conform to wrist and finger contour with the fingers extended in natural condition.

3 Claims, 19 Drawing Sheets

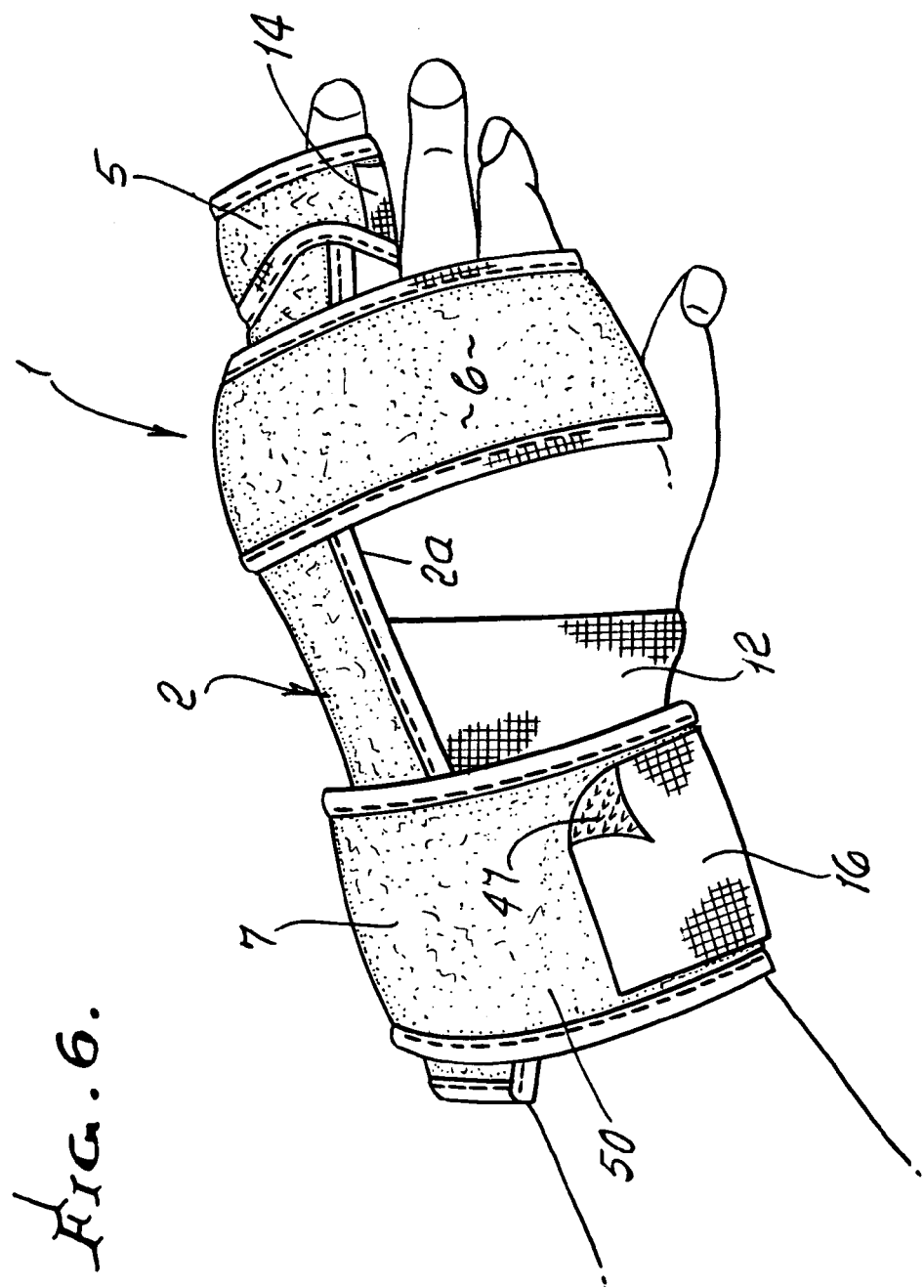

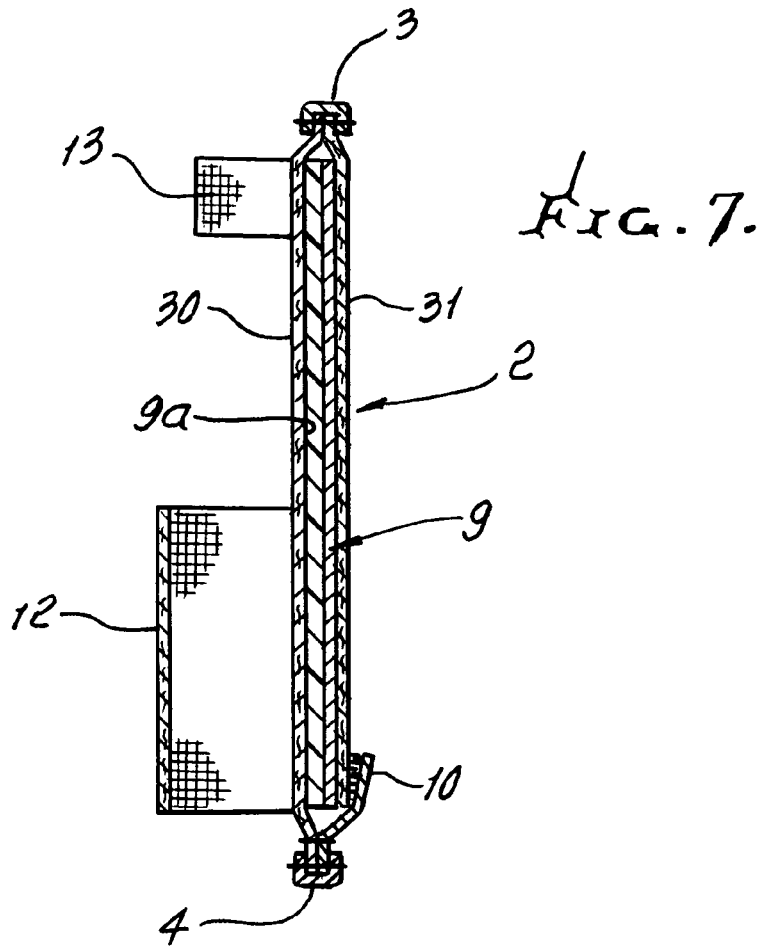
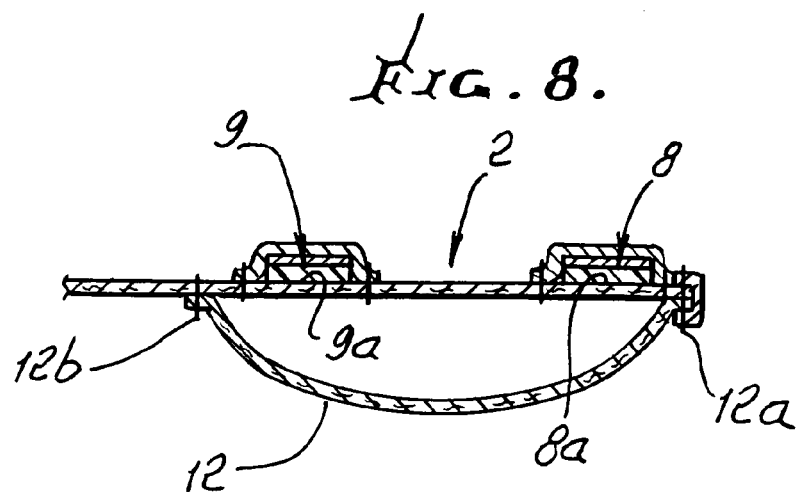

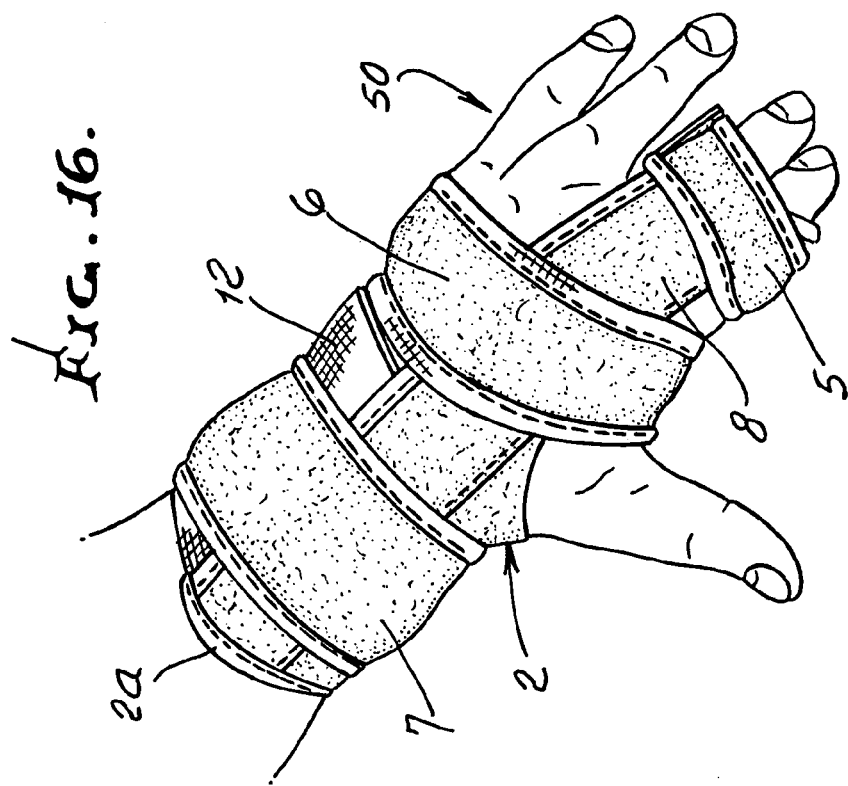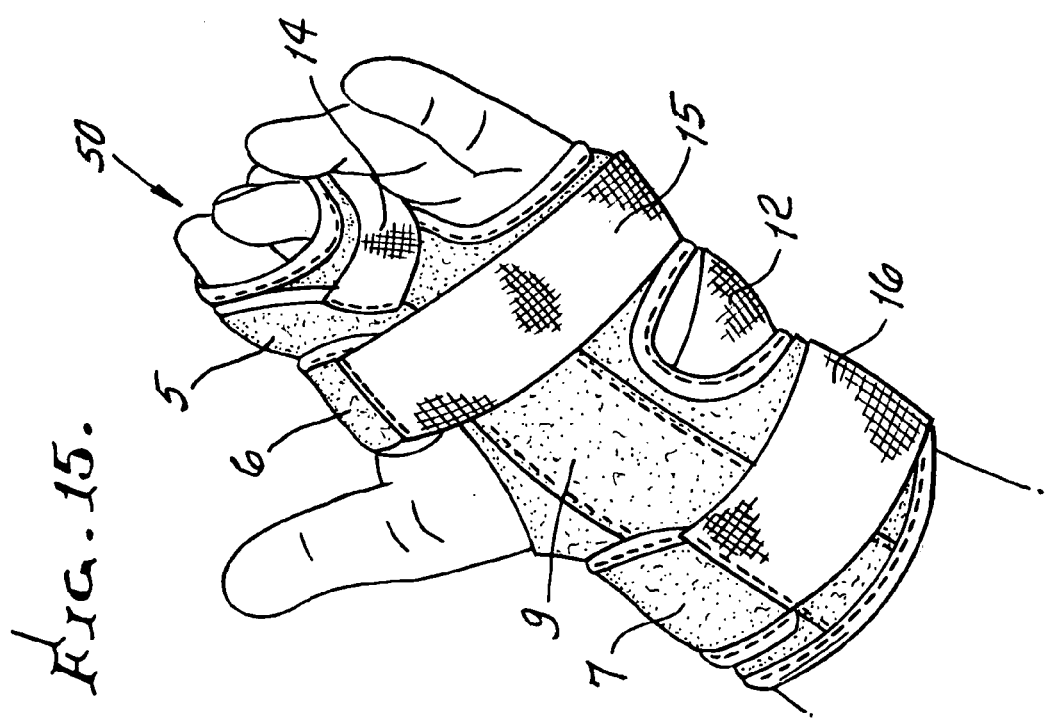

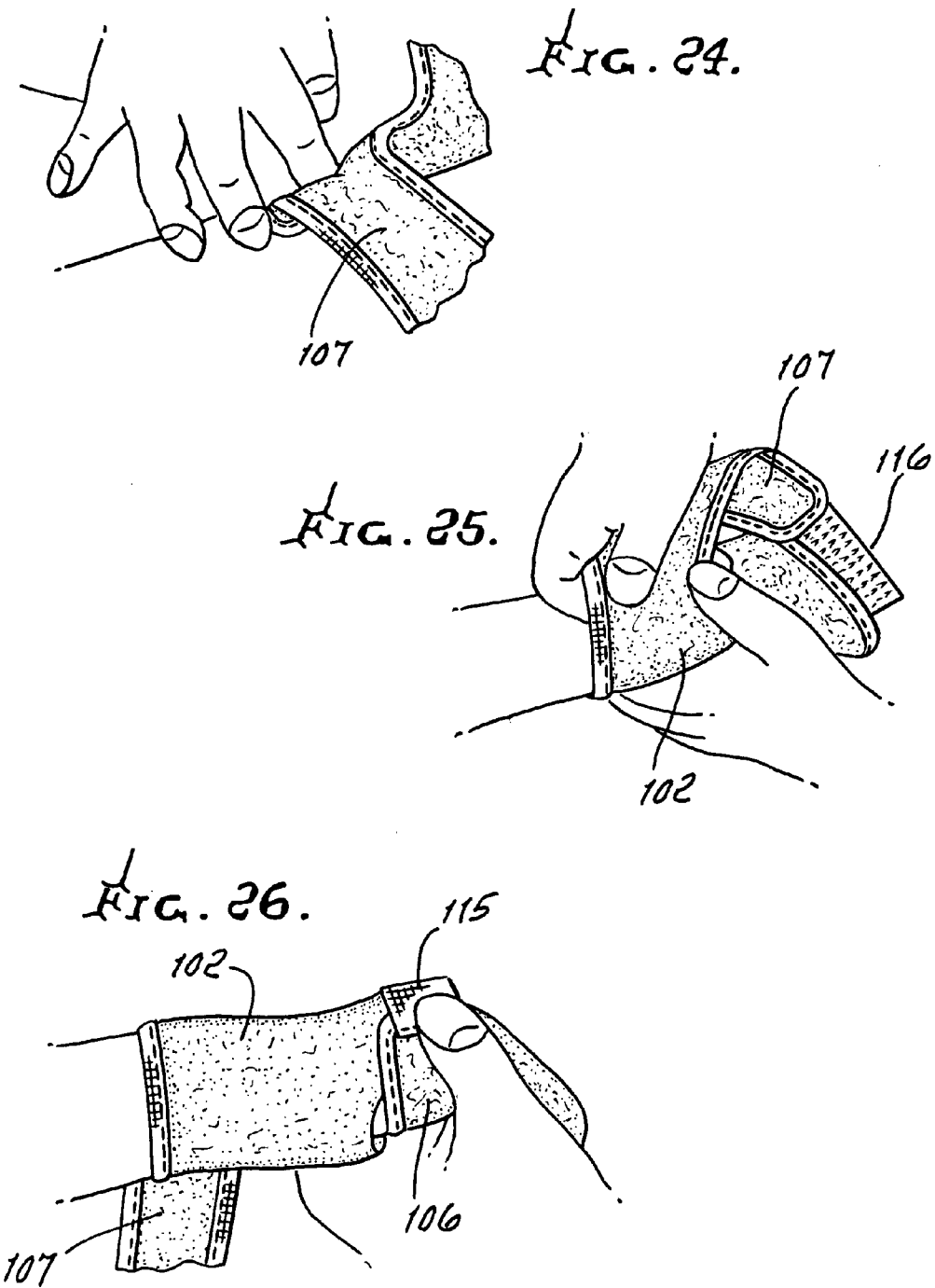

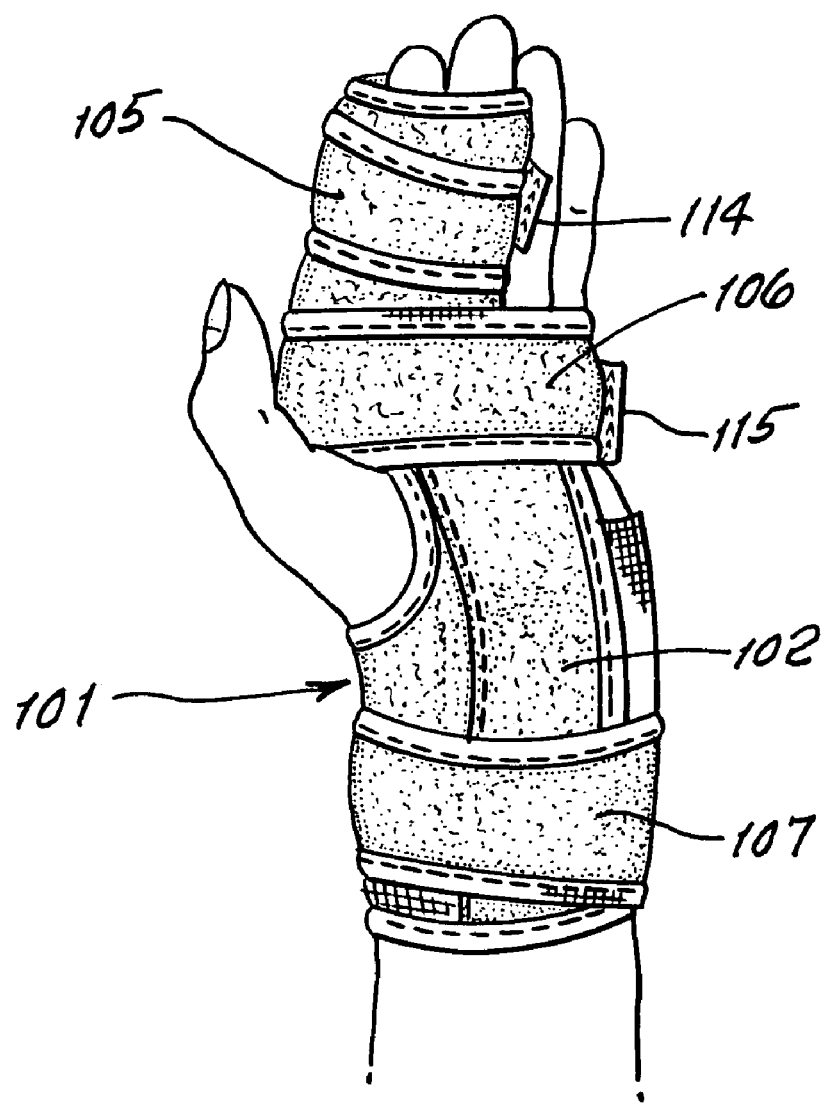

HAND BRACE

This application is a divisional of U.S. application Ser. No. 11/097,071, filed Apr. 4, 2005, now U.S. Pat. No. 7,278,980, issued on Oct. 9, 2007 which is a continuation-in-part of pending U.S. application Ser. No. 10/856,304, filed Jun. 1, 2004 now U.S. Pat. No. 7,276,039, issued on Oct. 2, 2007.

BACKGROUND OF THE INVENTION

The present invention relates generally to a hand, wrist and finger brace, one example being a boxer's fracture brace. More particularly, the present invention relates to an improved brace for temporarily immobilizing the hand in such a way as to allow a fracture of the neck of the fourth, ring finger, or fifth metacarpal, which is the bone in the small finger of the human hand, to heal in a desired manner, with a minimum of disruption in the patient's normal activity.

There are over 1,500,000 metacarpal and phalangeal fractures each year. A large percentage of these involve a fracture of the fourth or fifth metacarpal shaft and neck. This injury is commonly known as a "boxer's fracture", as it is often the result of someone striking or punching an object harder than the hand, such as a wall or another person's head as during boxing. The traditional treatment for such an injury is three to six weeks of cast immobilization. Due to how these types of injuries occur, they are often experienced in younger, more active individuals. In such patients, there is a high desire and need to return to work and/or physical and athletic activities as quickly as possible. Therefore, there exists a need for treatment of these types of injuries in such a way as to allow an accelerated return to normal activities by the patient in an easy and hand flexible manner.

SUMMARY OF THE INVENTION

The present invention relates to a new, useful and unique hand immobilizing brace that is useful for a large group of patients based upon it's ease of application to the hand, and its moldability to the hand, its flexibility, reversibility and improved healing promotion capabilities. These features will meet a need not currently being met and for the foregoing reasons, this invention is intended to fill this void.

The invention is also directed to a brace enabling a patient to quickly return to normal work and/or physical activities. The versatile, moldable brace is typically configured to immobilize the fourth and fifth metacarpal fractures as well as phalangeal fractures, while at the same time being easily removable from the patient.

It is a further object of this invention that the brace be readily conformable or moldable to easily fit a large number of patients' hands through the use of semi-rigid inserts received in elongated pockets in an elongated brace body. The inserts are positioned to facilitate reversibility of the brace, for use on a fracture of either hand.

A further object is to provide an improved finger and hand brace that preferably includes:

a) a longitudinally elongated brace body, adapted to be applied lengthwise to the wrist and finger regions of the hand, b) multiple flexible flaps carried by the body to be spaced lengthwise thereof and to extend from the body, c) separate flaps configured to be securely wrapped about at least two of the following:
  i) hand
  ii) wrist
  iii) a finger or fingers, d) retention means on the brace to retain the flaps in wrapped condition, e) and two generally longitudinally elongated stiffeners carried by said body, said stiffeners having undulating extent or extents, to readily conform to wrist and finger contour with the fingers extended in natural condition.

As will be seen, such stiffener undulating extents include a concave curvature, defined for example by one stiffener, to conform to palm curvature; convex curvature, defined by a second stiffener, to conform to knuckle curvature.

Another object is to provide pockets in the body to receive the stiffeners, two of the straps positioned to be wrapped about both pockets, stiffeners therein, and body material associated therewith, to hold said undulating extents near the palm and knuckle, respectively in wrapped condition of the brace. In this regard the pockets undulate in conformance with said stiffener undulating extents.

An added object is to provide an elongated opening in the body, between said undulating extents, to receive the user's thumb.

These and other objects and advantages of the invention, as well as the details of an illustrative embodiment, will be more fully understood from the following specification and drawings, in which:

DRAWING DESCRIPTION

FIG. 4 is a view like FIG. 3, but showing one strap in finger securing position;

FIG. 6 is a view like FIG. 5, but showing all straps wrapped in securing position;

FIG. 7 is a section taken on lines 7-7 of FIG. 1;

FIG. 8 is a section taken on lines 8-8 of FIG. 2;

FIGS. 9-18 are views showing the brace of the invention applied to left and right hands that have undergone fractures;

FIGS. 24-26 are views showing optimal step-by-step application to relieve pressure on the ulnar styloid; and FIGS. 27-31 are views showing step-by-step application of the brace to the fingers, hand, and wrist, as used in radial gauntlet applications.

DETAILED DESCRIPTION

Figure 1:
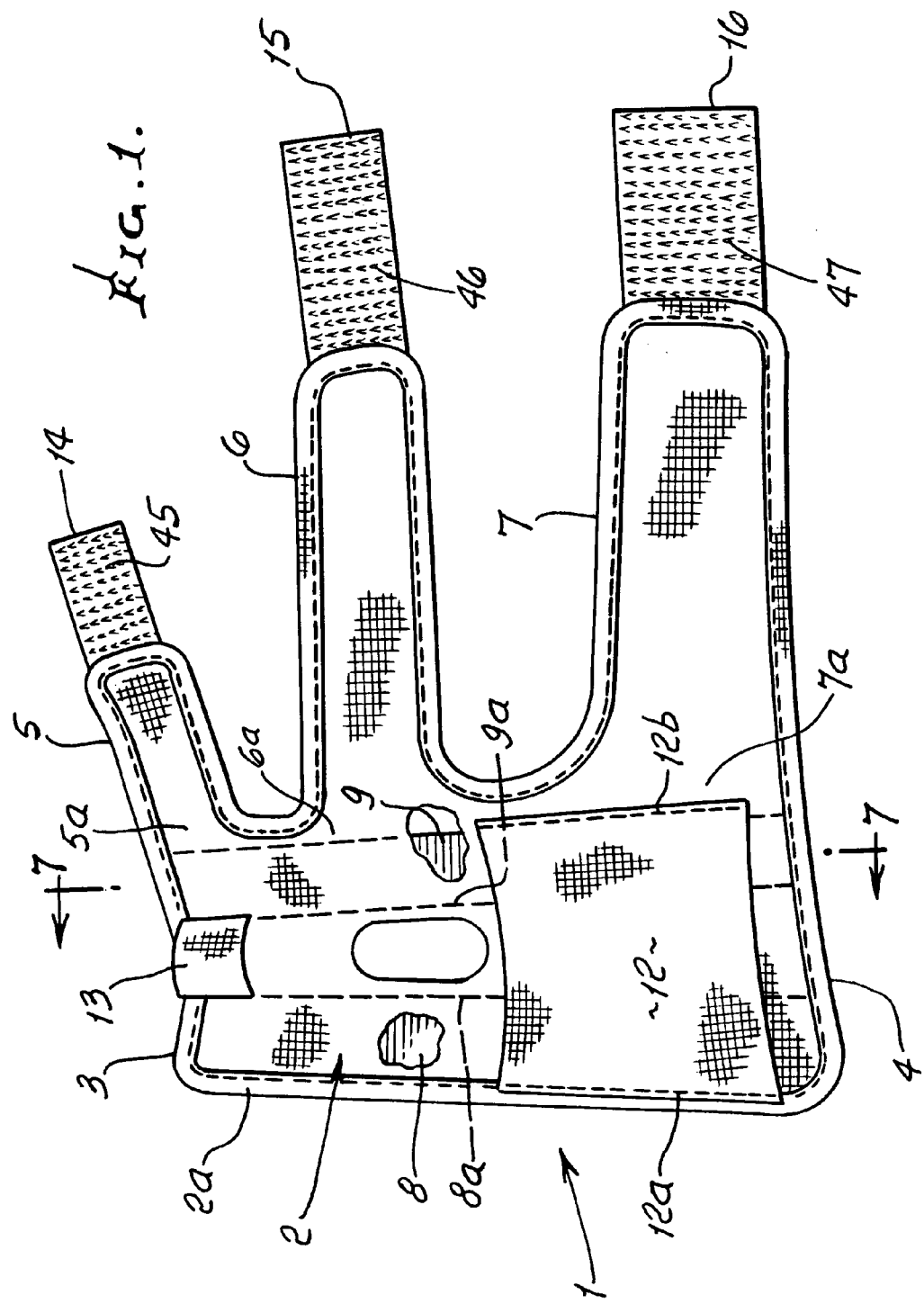
FIG. 1 shows one side of a preferred embodiment of the brace.

Referring now to FIGS. 19-31, showing the preferred brace and its use, the unfolded i.e. unwrapped brace 101 has an elongated body or member 102 having a distal end 103 and a proximal end 104.

Three or more straps 105-107 are provided, and positioned along the elongated member 102 to secure a patient's fingers and hand, respectively, to member 102. In this embodiment, the brace is made of a flexible webbing material commonly known in the medical industry, and may have seam binding material 102a extending at the periphery of 102, in bounding relation.

Rigidity for the brace 101 as needed for hand immobilizing is provided by two slat-like elongated stiffeners or inserts 108 and 109 that are inserted in longitudinally elongated and cushioned pockets 108a and 109a on or in the webbing that extends between outer edges of the elongated body member 102, and between the distal end 103 and the proximal end 104. In this embodiment the inserts may be approximately one inch wide and may consist of moldable or malleable (adjustably bendable), semi-rigid metal such as aluminum. One or both inserts can be removed as via slots secured by flaps 110 and 111 located at the ends of the pockets at the proximal ends of the elongated members. The flaps 110 and 111 are typically held in closed position by a VELCRO system, or similar hook and pile system. In closed position, the flaps maintain the inserts securely in the pockets in brace 101. Retention of the semi-rigid inserts as described also further enhances the ability of the brace to be reversible, so it can be applied to either the left or right hand of a patient, with no need for two separate braces. For this purpose, the opposite side walls of the pockets are cushioned, as seen at 30 and 31 in FIG. 7.

In accordance with an important aspect of the invention, the typically metallic stiffeners or inserts have undulating extent or extents to readily conform to wrist and finger contours, with user's fingers extended in natural contour. Knuckle contour is typically of most importance as respects matching contour of a first stiffener 108.

Figure 19A:
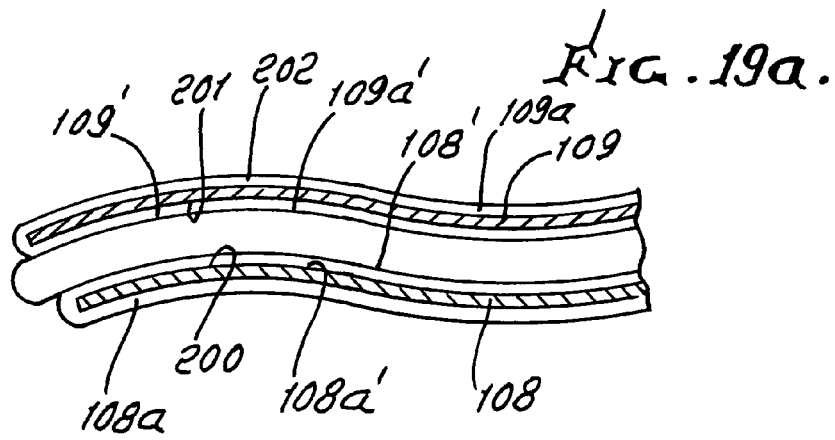
FIG. 19a is a schematic view showing positioning of stiffener undulations after wrap-folding of the brace.

The undulating extents of the stiffeners or inserts include, as shown in FIG. 19a,
  i) an upwardly convex curvature 200 of 108 (in unfolded condition of the brace), to conform to downwardly concave palm curvature after wrap-folding of the brace to bring the stiffener 108 under the palm and fingers,
  ii) and a downwardly concave curvature 201 of 109 to conform to upwardly convex knuckle contour 202 in wrap-folded condition of the brace.

After wrap-folding of the brace, and as substantially shown in FIG. 19a, curvature 200 of stiffener(s) 108, and its layer 108a' of associated pocketing 108a, lie directly beneath the user's palm curvature 108'; and concave curvature 201 of stiffener(s) 109, and its layer 109a' of associated pocketing 109a lie directly above the user's knuckle top curvature 109'.

Figure 19:
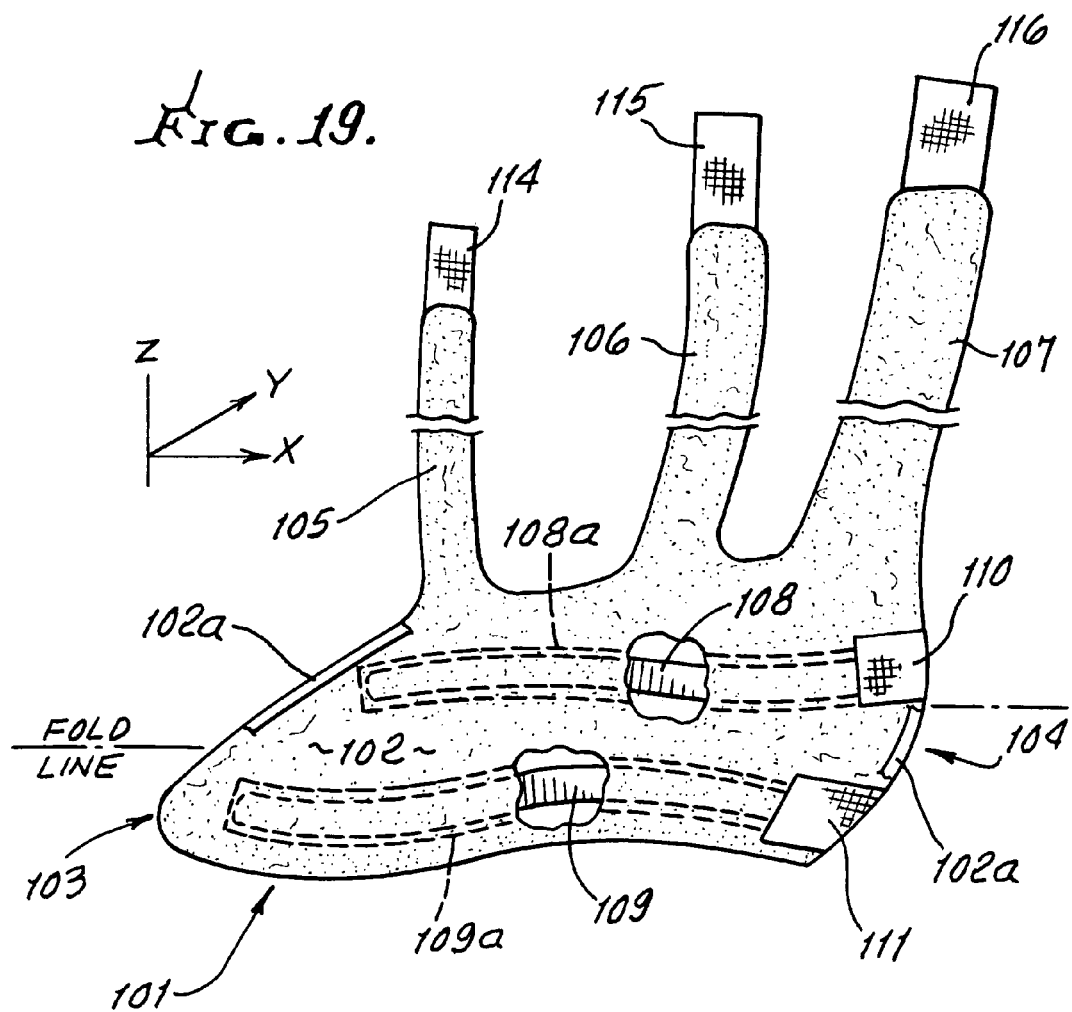
FIG. 19 is a schematic perspective view of two elongated stiffeners, and associated brace body material, prior to wrapping of the brace about the hand and wrist.
Figure 20:
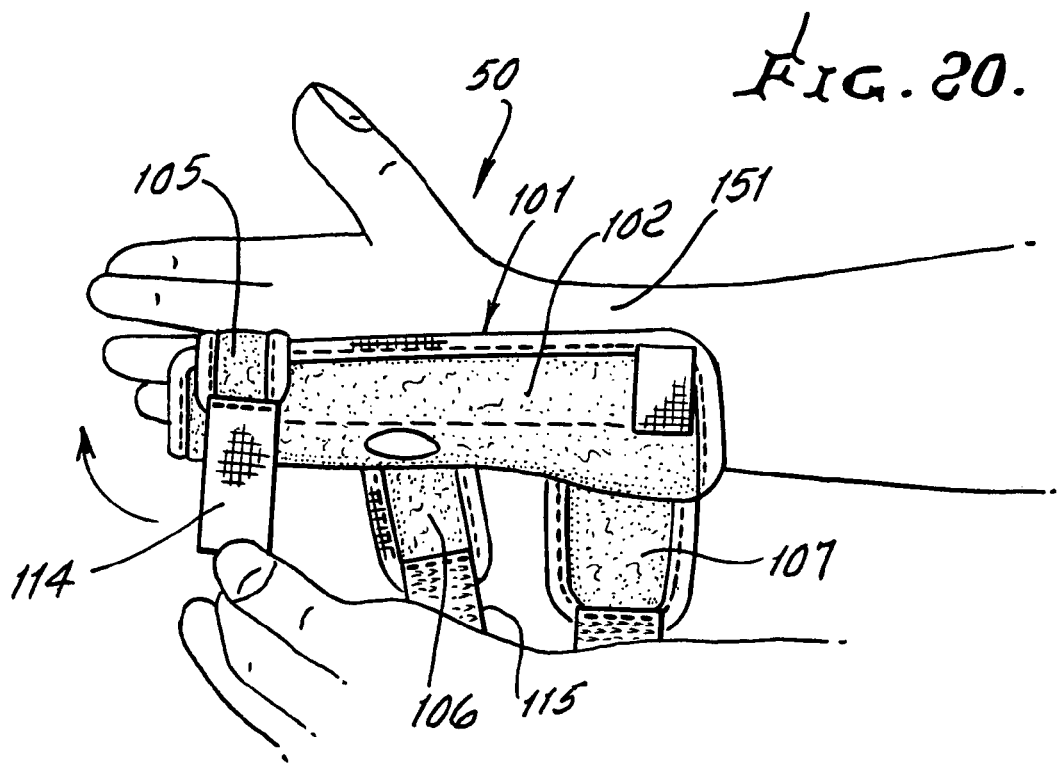
FIGS. 20-23 are views showing step-by-step application of the brace to the fingers, hand and wrist, and in a boxer fracture application.
Figure 23:
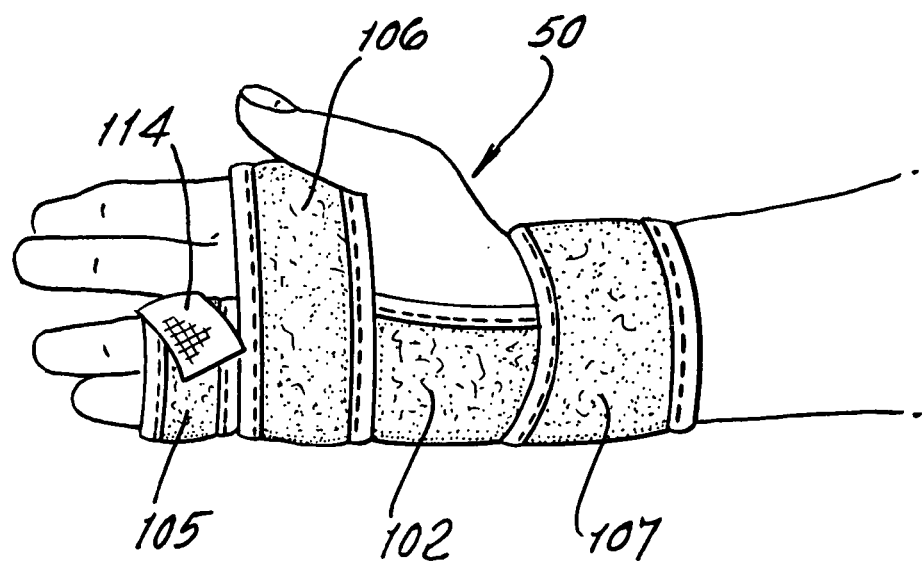

The straps 105, 106, and 107 shown as laterally elongated in FIG. 19, can be of any fixable and flexible material, and retained in wrapped condition as shown in FIGS. 20 and 23, and also in FIGS. 24-26. Note that strap 106 is narrower than strap 107. Each strap has a locking mechanism at its terminal to vary the length of the strap to fit or wrap around the hand, wrist, and fingers of a particular patient. As shown, the locking mechanism comprises hook or pile material on tabs 114-116, to press connect to pile or hook material on the back sides of the straps and/or body. That back side material is extensive in area to allow substantial variability in tab connection locations, accommodating to different hand sizes. It will be understood by those skilled in the art that the straps and the locking mechanisms are just one of a group of equivalent devices, for example, VELCRO straps, elastic straps, etc., and all such equivalents are deemed within the scope of the present invention.

As shown in FIG. 20, brace 101 is placed on a patient by first inserting the patient's hand 151 sidewise into the U-folded brace body. In this position the stiffeners of the brace are located at opposite sides of the hand. Further in this illustration, none of the straps 105-107 have yet been completely secured.

Figure 21:
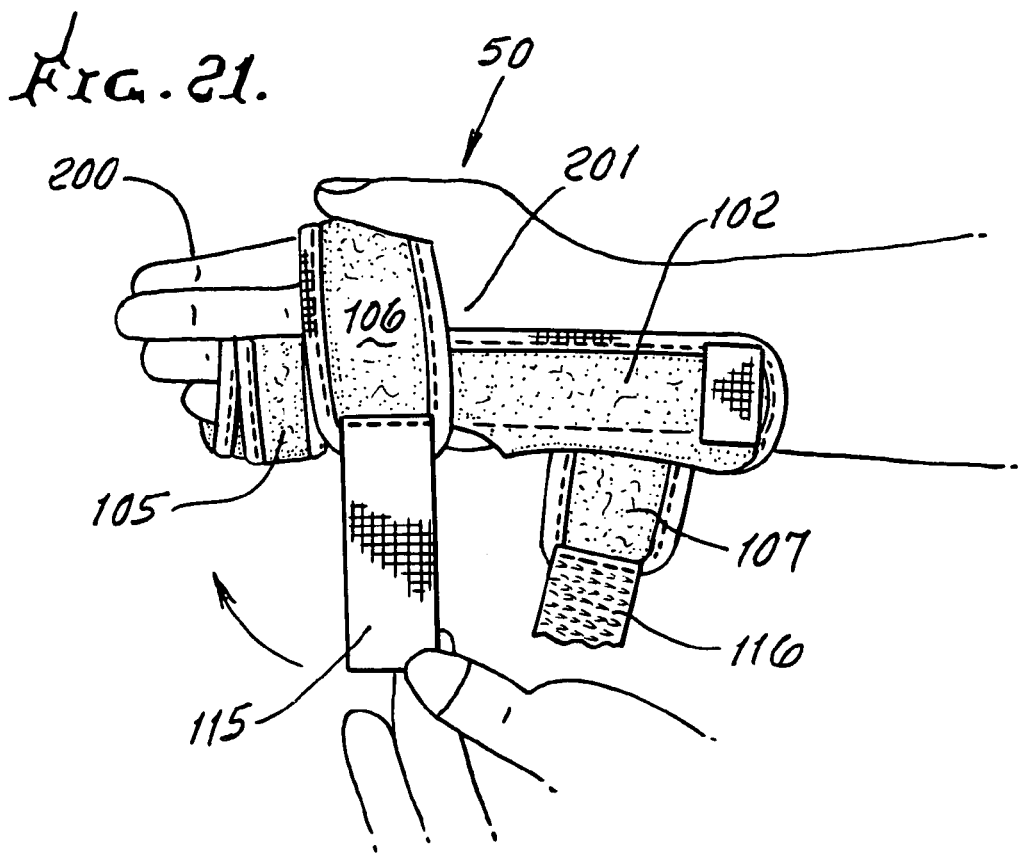
Figure 22:
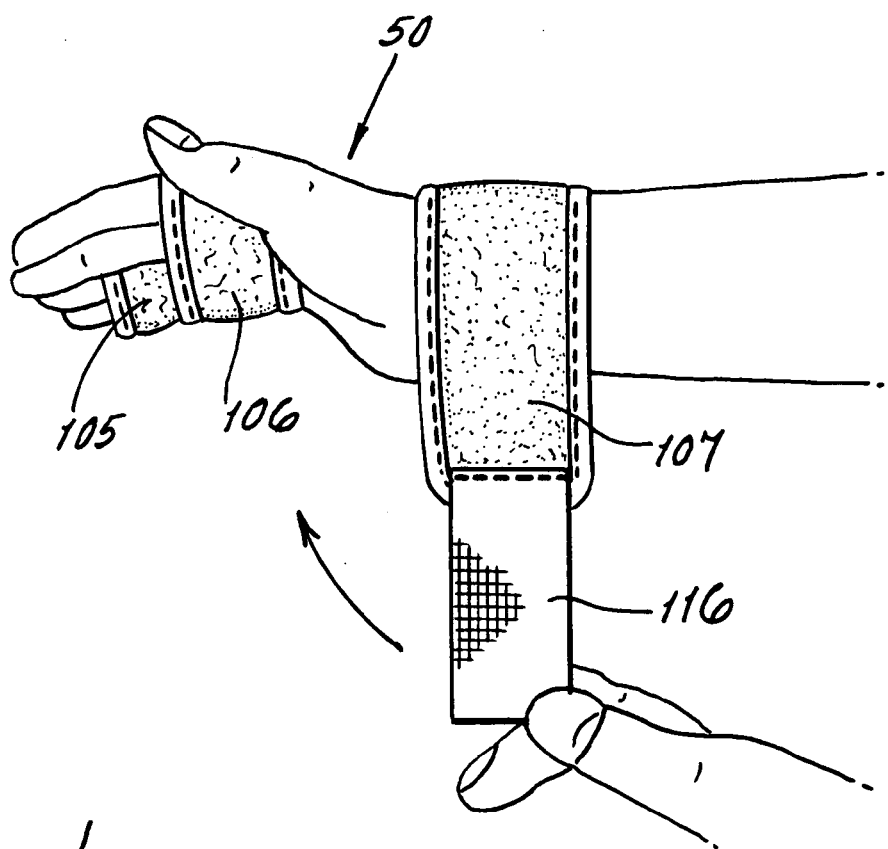

FIG. 20 shows brace 101 further secured to the patient by wrapping strap 105 around the pinky and ring fingers of the patient's hand, and securing it to the elongated body member 102, by locking mechanism 114. FIG. 21 shows brace 101 further secured to the patient by wrapping narrow strap 106 over the forefinger 200 and across the palm 201 and around the brace folded webbing or body 102, and it is then secured by securing locking mechanism 115 to material 102. See also FIG. 23. As shown in FIGS. 22 and 23, the brace is further completely secured or anchored to the patient by wrapping strap 107 around the lower arm or wrist of the patient and securing it to the elongated member 102 by locking mechanism 116 applied to 102. Strap 107 and the stiffeners brace the hand, and anchor the wrist in fixed positions. The three straps are quickly and easily removable, for hand adjustment. Optional strap wrapping is shown in FIGS. 24-26 to achieve ulnar styloid pressure relief.

In examples, the elongated member 102 may be approximately eight and one/half inches long, and six inches wide across the hand, and three inches wide across the fingers. The two semi-rigid inserts or stiffeners may consist of moldable aluminum, to be encased along the volar and dorsal aspects of the brace (one on each side), measuring about eight inches in length, and one inch in width.

The first strap 105, may be about three-fourths inches wide, and eight inches long, and attached to the dorsum of the proximal end for circumferential support as described. The narrowed second strap 106 may be about one and one eighth inches wide and thirteen and one-half inches long and is attached to the dorsal middle one third of the brace. It wraps around the palm, reattaching to the dorsal side of the brace 1. The third strap 107 is attached at the dorsal side of the proximal end and provides circumferential support to the wrist area, and is preferably about one and one-half inch wide and thirteen and one-half inches long.

In summary the finger and hand brace include:
  a) a longitudinally elongated brace body, adapted to be applied lengthwise to the wrist and finger region of the hand,
  b) multiple flexible flaps carried by the body to be spaced lengthwise thereof and to extend from the body,
  c) separate flaps configured to be securely wrapped about at least two of the following:
    i) hand
    ii) wrist
    iii) a finger or fingers,
  d) retention means on the brace to retain the flaps in wrapped condition,
  e) and two generally longitudinally elongated stiffeners carried by said body, said stiffeners having undulating extent or extents, to readily conform to wrist and finger contours with the fingers extended in natural condition.

Also provided is or are retention means located at flap terminals. Such retention means may comprise tabs projecting from flap terminals; and such tabs may include or carry hook or pile material. Sleeves are provided on the body to receive and position the user's wrist and at least one finger, to be wrapped by flaps.

It will be understood that the brace of the invention is applicable to either the left hand, or right hand, in various fracture modes as for example boxer fractures of the hand. For example, FIGS. 20-23 are views showing the brace of the invention applied to the right hand 50 that has undergone a boxer fracture. The view (metacarpal 4 and 5) is otherwise described as a "left lateral, outside". A boxer fracture may be described as a traumatic fracture of the fifth metacarpal bone, at the shaft and neck of that bone. Such a fracture usually results from punching activity. Note strap 106 wrapped about the palm of the hand; strap 105 wrapped about the pinky and ring fingers, and strap 107 wrapped about the wrist.

FIGS. 27-31 show the brace of the invention (FIGS. 19 and 19a) applied in gauntlet mode to the left hand of the user. Elements of the brace bear the same identifying numerals, as in FIGS. 20-23.

In gauntlet mode, the brace can be used to immobilize metacarpal 4 and/or 5 and proximal phalange or phalanges 4 and/or 5 on the right hand, and metacarpal 2 and/or 3 and proximal phalange or phalanges 2 and 3 on the left hand. When turned over, the reversible brace can be used to immobilize metacarpal 4 and/or 5 and proximal phalange or phalanges 4 and 5 on the left hand, and metacarpal 2 and/or 3 and proximal phalange or phalanges 2 and/or 3 on the right hand. Malleable stays in or on the brace are typically bent or re-bent to conform as in FIGS. 19 and 19a to the selected use, prior to application of the brace to the hand and wrist.

Figure 27:
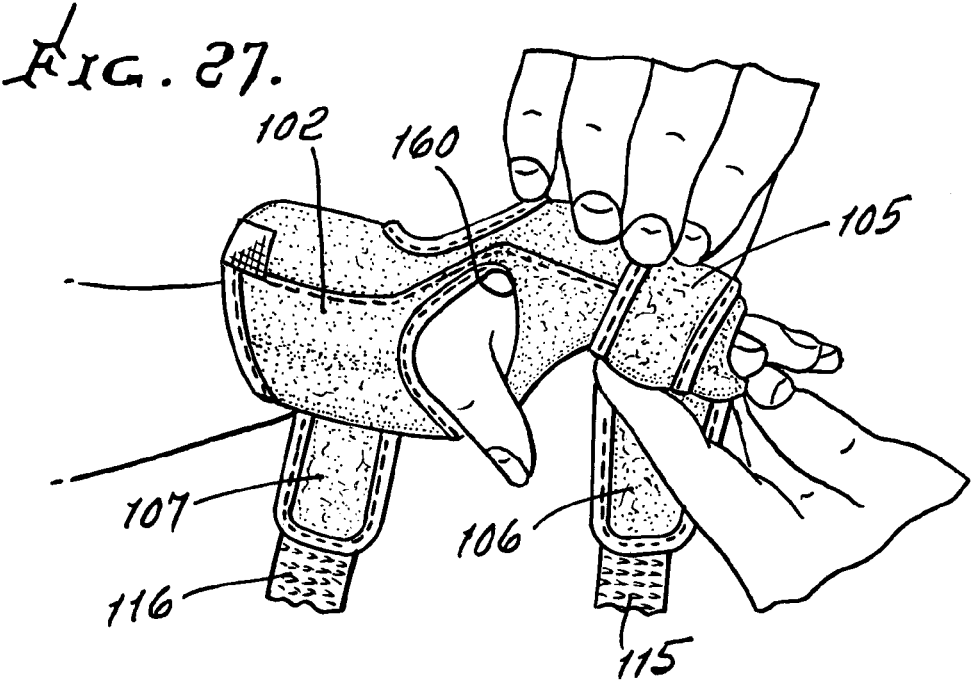
Figure 28:
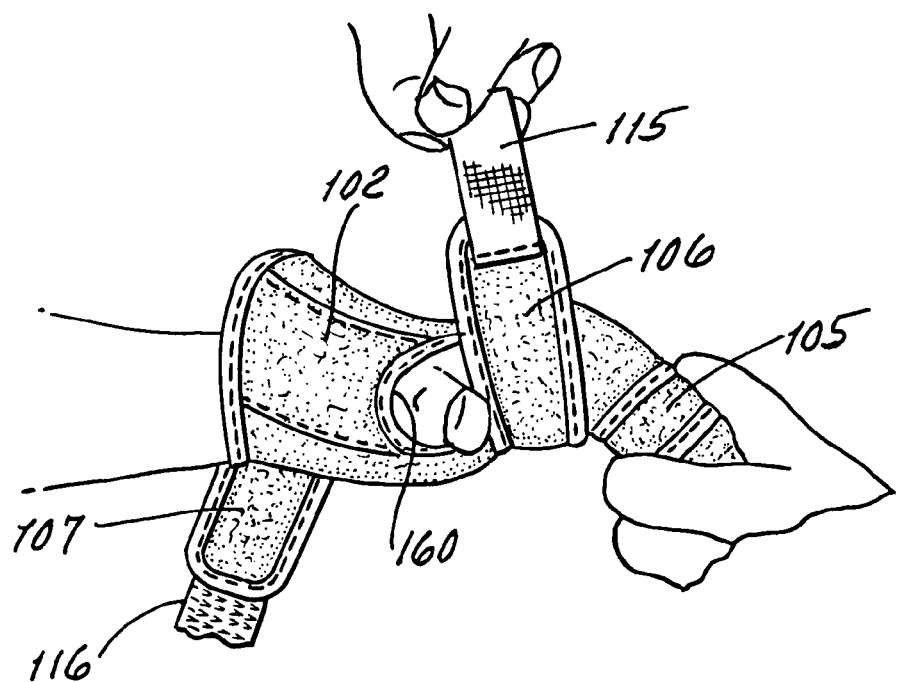
Figure 29:
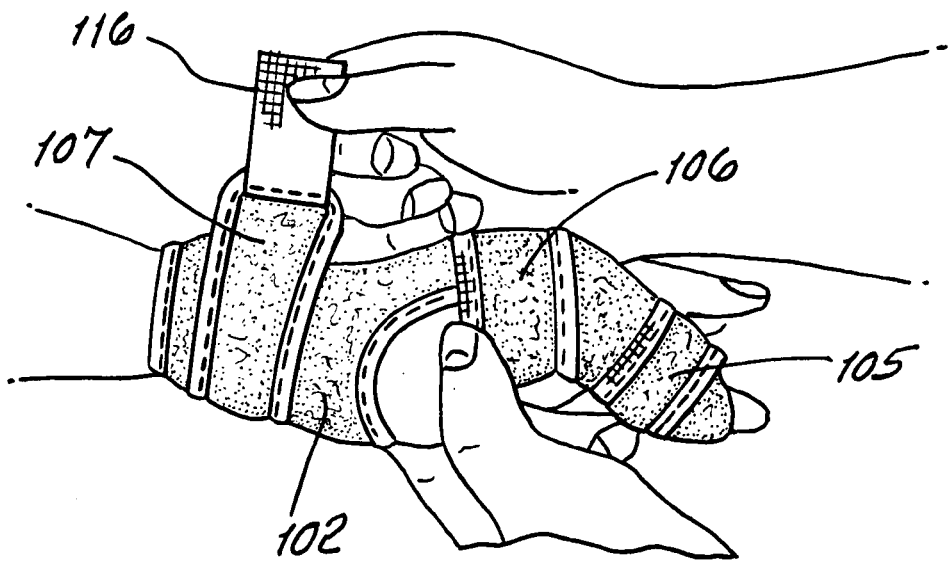
Figure 30:
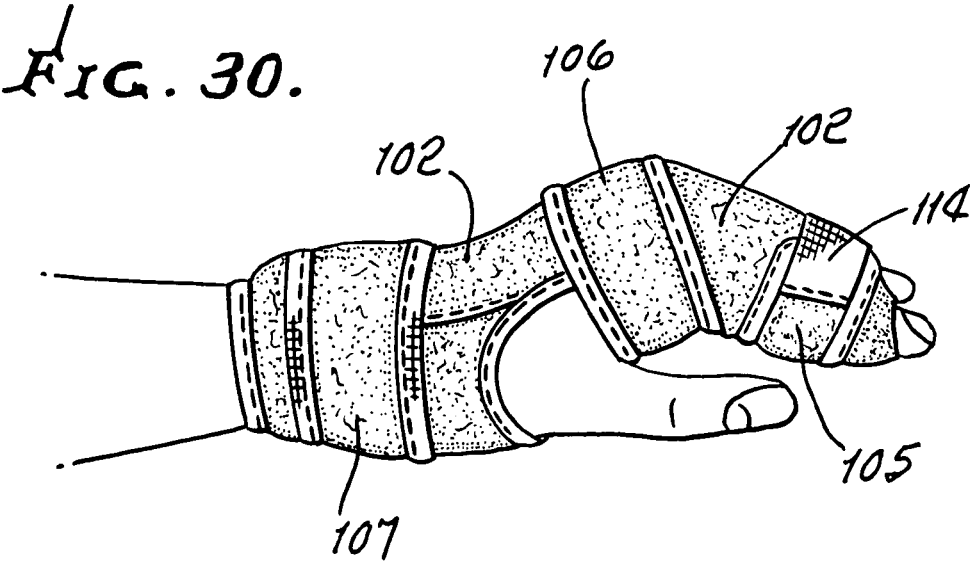

When using the brace for $4^{th}$ and $5^{th}$ metacarpal fractures, the thumb passing through opening 160 in body 102, between the stiffeners, in lateral alignment with 106, as seen in FIG. 27, is not used. However, when the brace is used for the $2^{nd}$ and $3^{rd}$ metacarpal fractures, the thumb opening receives the user's thumb.

Figure 2:
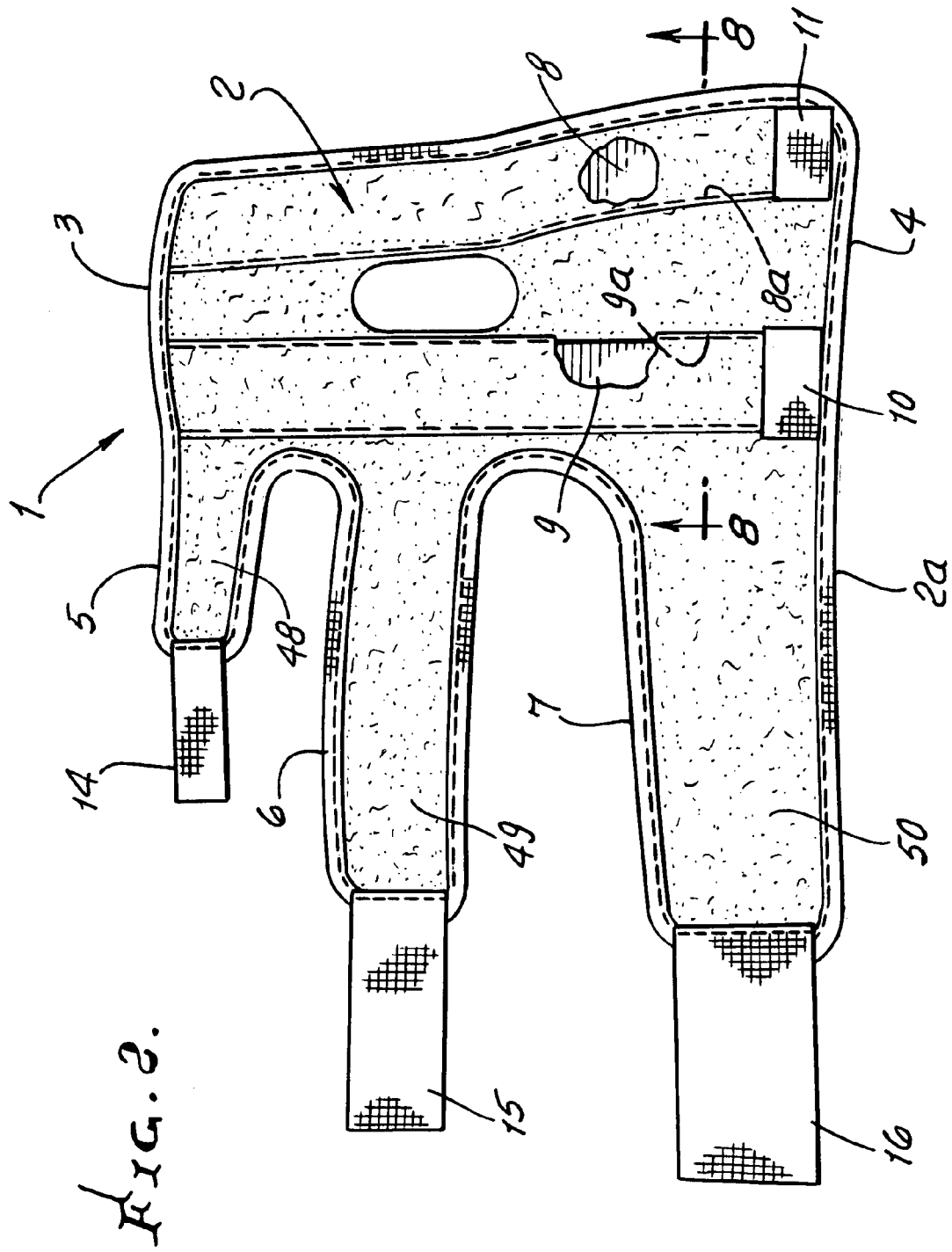
FIG. 2 shows the opposite side of the FIG. 1 brace.

FIGS. 1 and 2 depict two views of one preferred embodiment of the brace 1 of the present invention. FIG. 1 shows the interior view of the brace which is the side of the brace which is placed against the patient's hand and wrist. FIG. 2 shows the exterior view of the FIG. 1 brace which is the opposite side of the brace as shown in FIG. 1.

Brace 1 comprises a longitudinally elongated body or member 2, having a distal end 3 and a proximal end 4. Three or more straps, 5-7, are provided, and positioned along the elongated member 2 to secure a patient's fingers and hand, respectively, to member 2. In this embodiment, the brace is made of a flexible webbing material commonly known in the medical industry, and may have seam binding material 2a extending at the periphery of 2, in bounding relation.

Rigidity for the brace 1 as needed for hand immobilizing is provided by two slat-like elongated inserts 8 and 9 that are inserted in longitudinally elongated and cushioned pockets 8a and 9a on or in the webbing that extend between outer edges of the elongated body member 2, and from the distal end 3 to the proximal end 4. In this embodiment the inserts may be approximately one inch wide and may consist of moldable or malleable (adjustably bendable), semi-rigid metal such as aluminum. One or both inserts can be removed as via slots in the webbing secured by flaps 10 and 11 located at the ends of the pockets at the proximal ends 4 of the elongated members. The flaps 10 and 11 are typically held in closed position by a VELCRO system, or similar hook and pile system. In closed position, the flaps maintain the inserts securely in the pockets in brace 1. Retention of the semi-rigid inserts as described also further enhances the ability of the brace to be reversible, so it can be applied to either the left or right hand of a patient, with no need for two separate braces. For this purpose, the opposite side walls of the pockets are cushioned, as seen at 30 and 31 in FIG. 7.

The brace also carries a sleeve 12 connected at 12a and 12b to the elongated body member 2 near the proximal end 4, such connections extending toward the distal end 3, whereby the sleeve captivates and positions the patients inserted wrist and/or lower hand to provide further stability of the proximal end of the brace relative to the hand and wrist. A smaller sleeve 13 may be provided at or near the distal end 3 of the elongated body member, at or near the center of the elongated body member, and into which the patient's pinky finger is placed or inserted to provide further stability of the fifth metacarpal and the distal end of the brace.

The straps 5, 6, and 7 shown as laterally elongated in FIG. 1, can be any fixable and flexible material, and retained to the member at 5a, 6a and 7a as shown in FIGS. 1 and 2. Each strap 5, 6 and 7 has a locking mechanism at its terminal to vary the length of the strap to fit the hand and wrist of a particular patient. As shown, the locking mechanism comprises hook or pile material 45-47 on tabs 14-16, to press connect to pile or hook material 48 to 50 on the back sides of the straps. Material at 48-50 is extensive in area to allow substantial variability in tab connection locations, accommodating to different hand sizes. It will be understood by those skilled in the art that the straps 5, 6, and 7 and the locking mechanisms 14, 15 and 16 are just one of a group of equivalent devices, for example, VELCRO straps, elastic straps, etc., and all such equivalents are deemed within the scope of the present invention.

Figure 3:
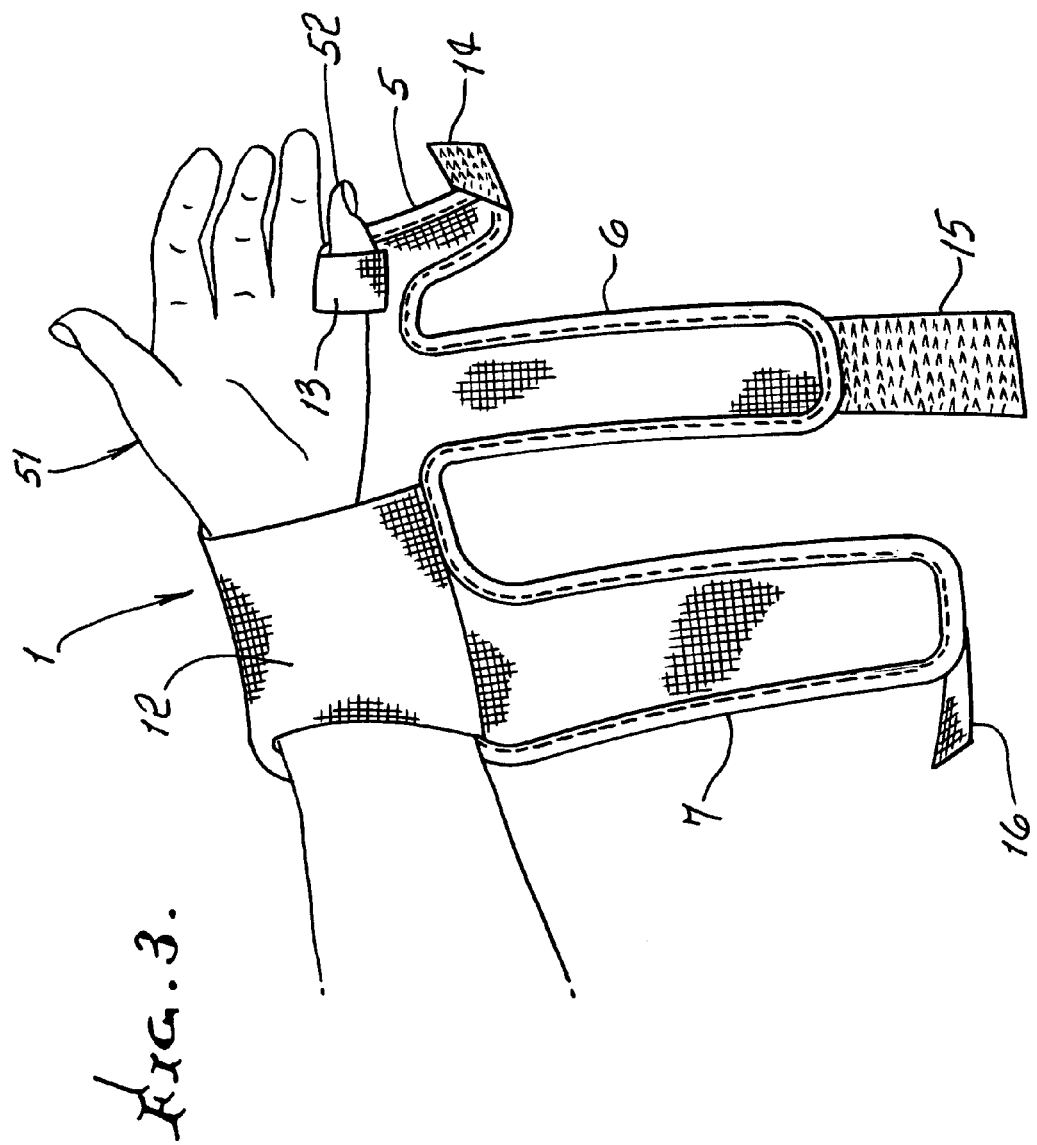
FIG. 3 is a view like FIG. 1, but also showing the brace being applied to a patient's hand.

As shown in FIG. 3, brace 1 is placed on a patient by first inserting the patient's hand 51 through or under sleeve 12 and then further inserting the patient's pinky finger 52 into sleeve 13. In this position the semi-rigid stiffeners of the brace are located on either side of the pinky finger and lower hand. Further in this illustration, none of the straps 5, 6 and 7 have yet been secured.

Figure 5:
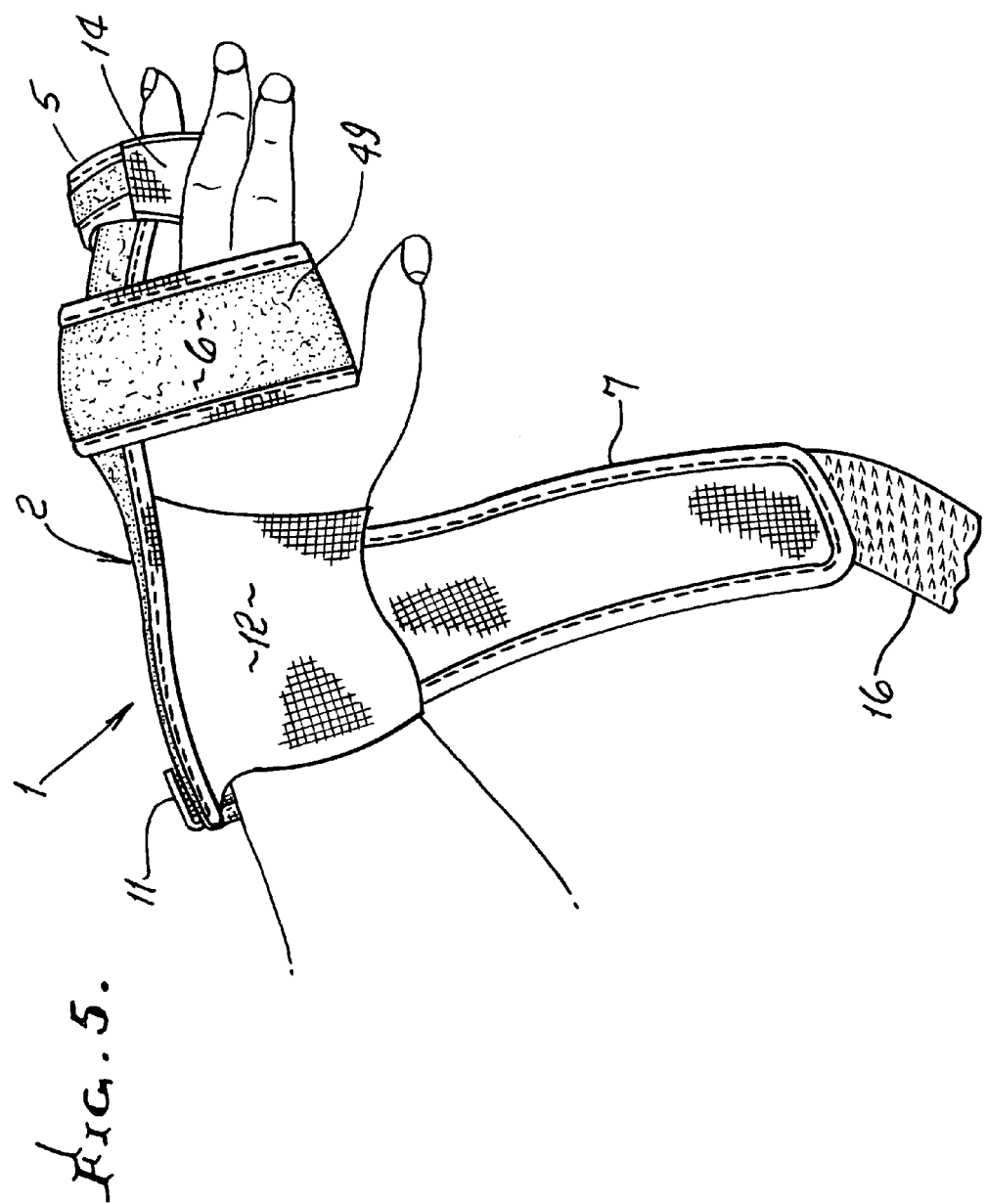
FIG. 5 is a view of the opposite side of the user's hand with two straps wrapped in position, and the third strap partially wrapped.
Figure 9:
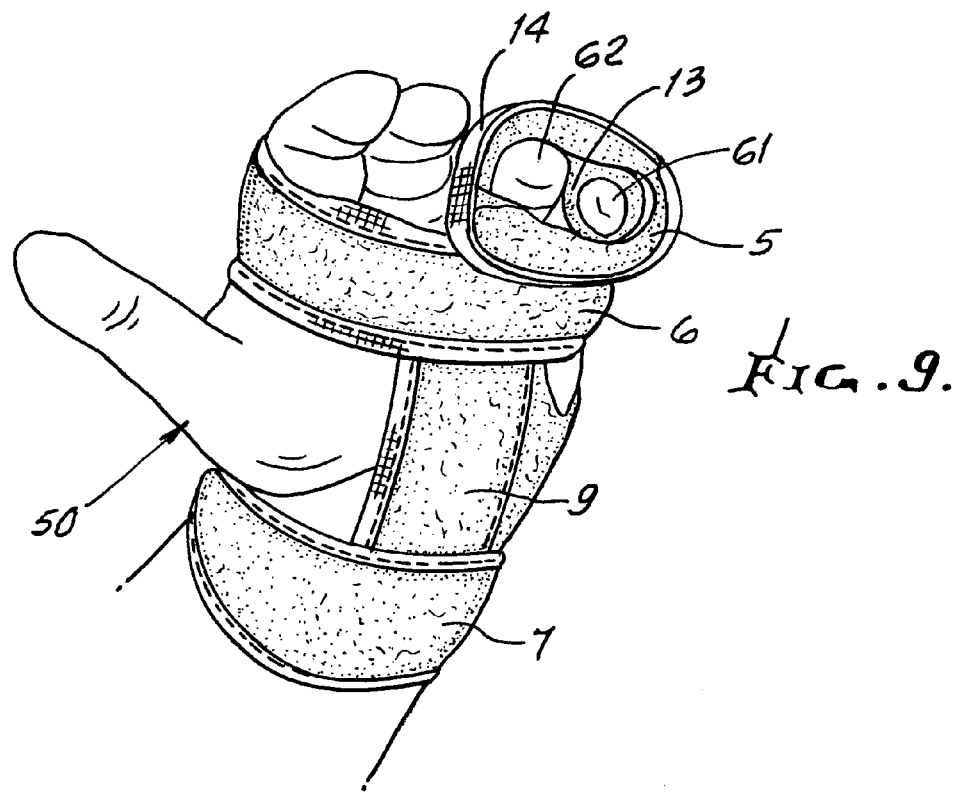

FIG. 4 shows brace 1 further secured to the patient by wrapping strap 5 around the pinky and ring fingers of the patient's hand, and securing it to the elongated member 2, by locking mechanism 14. FIG. 5 shows brace 1 further secured to the patient by wrapping strap 6 across the palm and around the webbing between the thumb and hand, and it is then secured to the elongated member 2 by securing locking mechanism 15 to material at 49. As shown in FIG. 6, the brace 1 is further completely secured or anchored to the patient by wrapping strap 7 around the lower arm or wrist of the patient and securing it to the elongated member 2 by locking mechanism 16 applied to 50. Strap 7 and the stiffeners brace the hand and anchor the wrist in fixed positions. The three straps are quickly and easily removable, for hand adjustment.

In an example, the elongated member 2 may be approximately eight and one/half inches long, and six inches wide across the hand, and three inches wide across the fingers. The two semi-rigid inserts may consist of moldable aluminum, to be encased along the volar and dorsal aspects of the brace (one on each side), measuring about eight inches in length, and one inch in width.

The first strap 5, may be about three-fourths inches wide, and eight inches long, and attached to the dorsum of the proximal end for circumferential support of the fourth and fifth fingers, the ring and pinky fingers. The second strap 6 may be about one and one eighth inch wide and thirteen and one-half inches long and is attached to the dorsal middle one third of the brace. It wraps around the palm, reattaching to the dorsal side of the brace 1. The third strap 7 is attached at the dorsal side of the proximal end and provides circumferential support to the wrist area, and is preferably about one and one-half inch wide and thirteen and one-half inches long.

In summary the finger and hand brace include:

a) a longitudinally elongated brace body, adapted to be applied lengthwise to the wrist and finger region of the hand, b) multiple flexible flaps carried by the body to be spaced lengthwise thereof and to extend from the body, c) separate flaps configured to be securely wrapped about at least two of the following:

i) hand ii) wrist iii) a finger or fingers, d) and retention means on the brace to retain the flaps in wrapped condition.

Three of such flaps are preferred, to wrap as referred to.

One or more longitudinally elongated stiffeners may be carried by said body; and a pocket or pockets are provided in the body to receive the stiffeners, two of the straps wrapping about two pockets and stiffeners therein. Such stiffeners are substantially inflexible.

Also provided is or are retention means located at flap terminals. Such retention means may comprise tabs projecting from flap terminals; and such tabs may include or carry hook or pile material. Sleeves are provided on the body to receive and position the user's wrist and at least one finger, to be wrapped by flaps.

Figure 9:
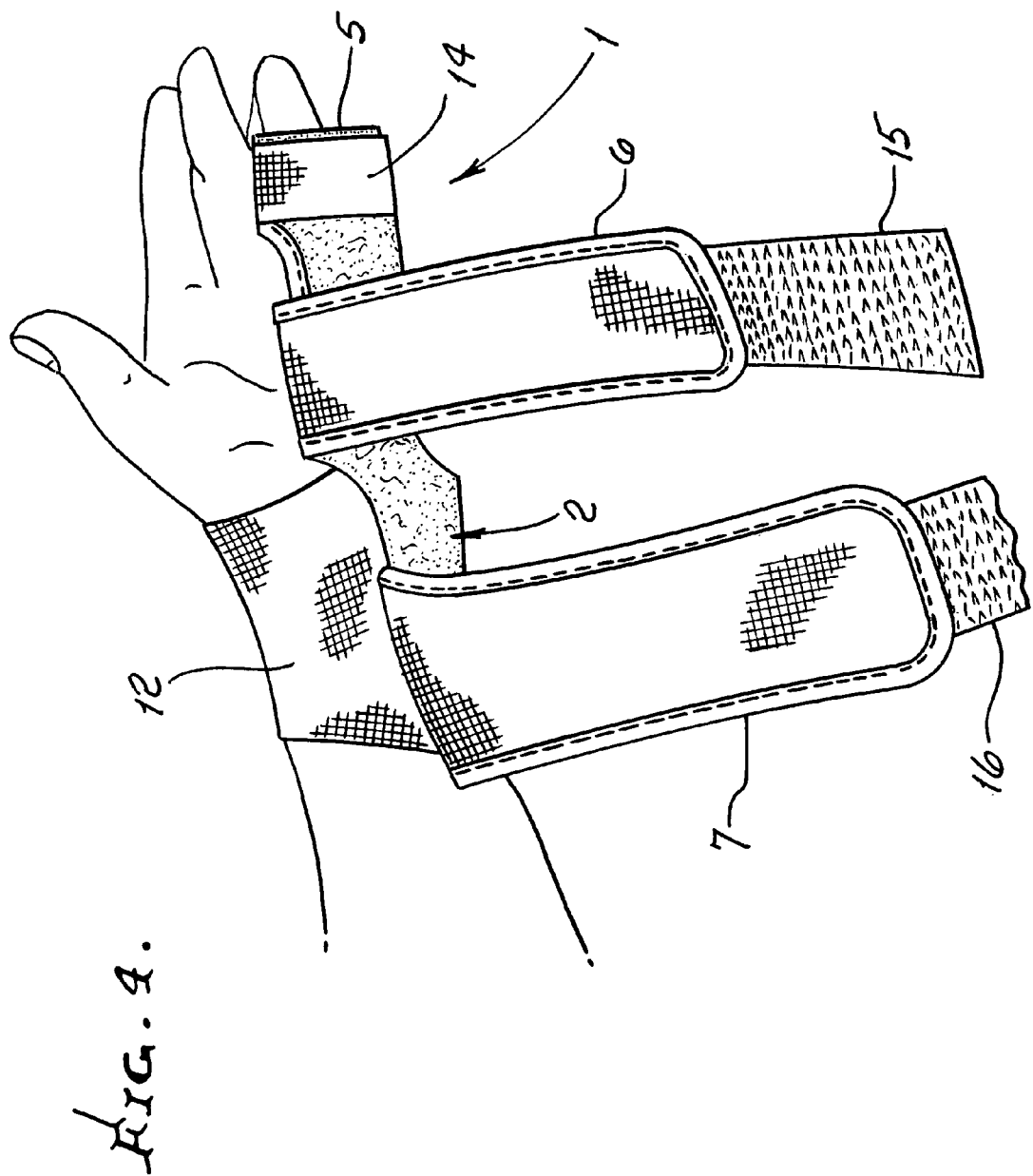
Figure 10:
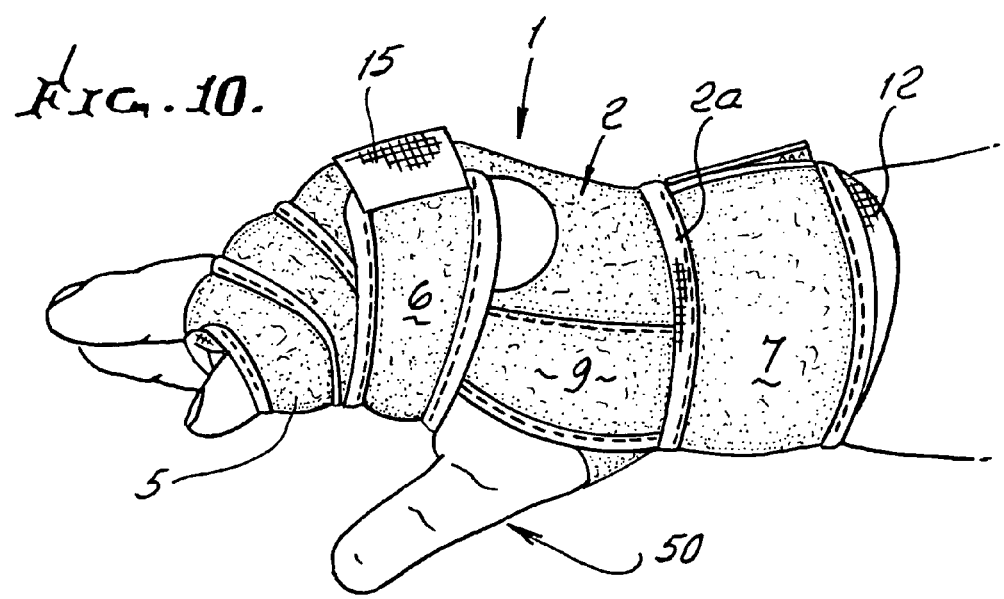
Figure 17:
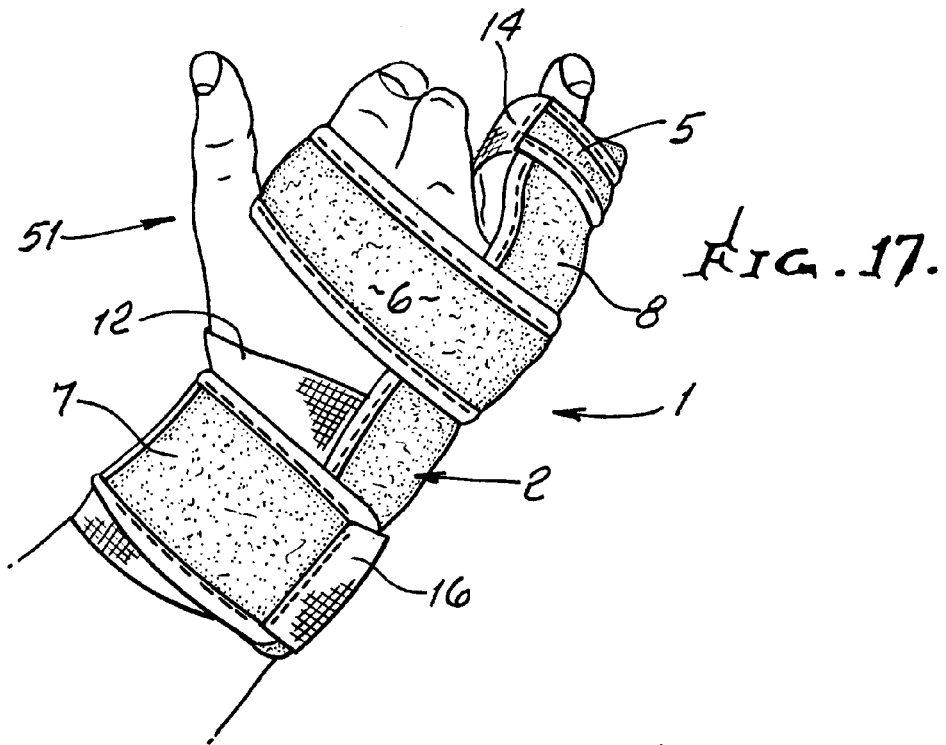

It will be understood that the brace 1 of the invention is applicable to either the left hand, or right hand, in various fracture modes. For example, FIGS. 9 and 10 are views showing the brace of the invention applied to the left hand 50 that has undergone a boxer fracture. The view (metacarpal 4 and 5) is otherwise described as a "left lateral, outside". A boxer fracture may be described as a traumatic fracture of the fifth metacarpal bone, at the shaft and neck of that bone. Such a fracture usually results from punching activity. Note strap 6 wrapped about the palm of the hand; strap 5 wrapped about the first and second fingers 61 and 62; and strap 7 wrapped about the wrist. FIG. 17 is another similar view.

Figure 11:
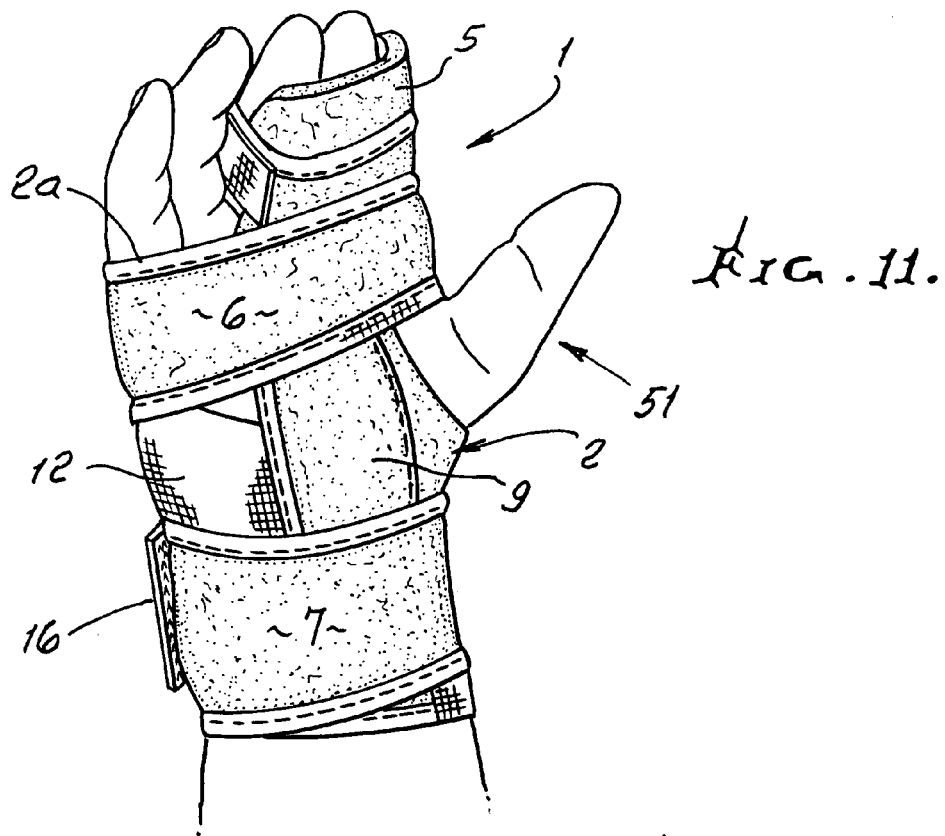
Figure 12:
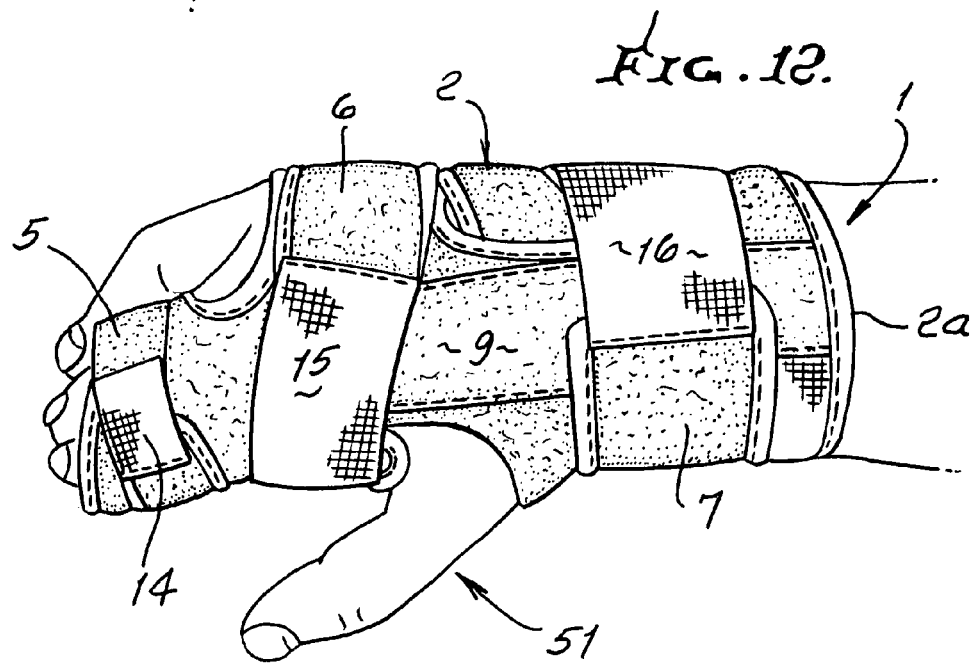
Figure 18:
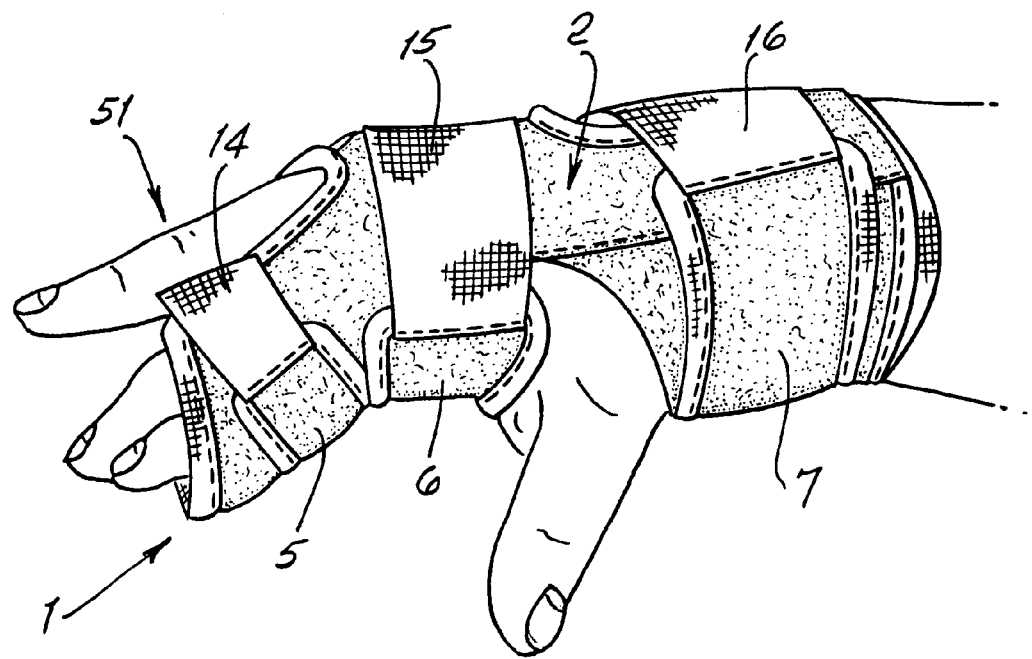

FIGS. 11 and 12 are views of the brace 1 applied to the right hand 51 that has undergone a metacarpal 2 and 3 fracture, the view otherwise referred to as a "right medial inside" view. Note the wrapped positions of the straps 5, 6, and 7, relative to the right hand 51. FIG. 18 is another similar view.

Figure 13:
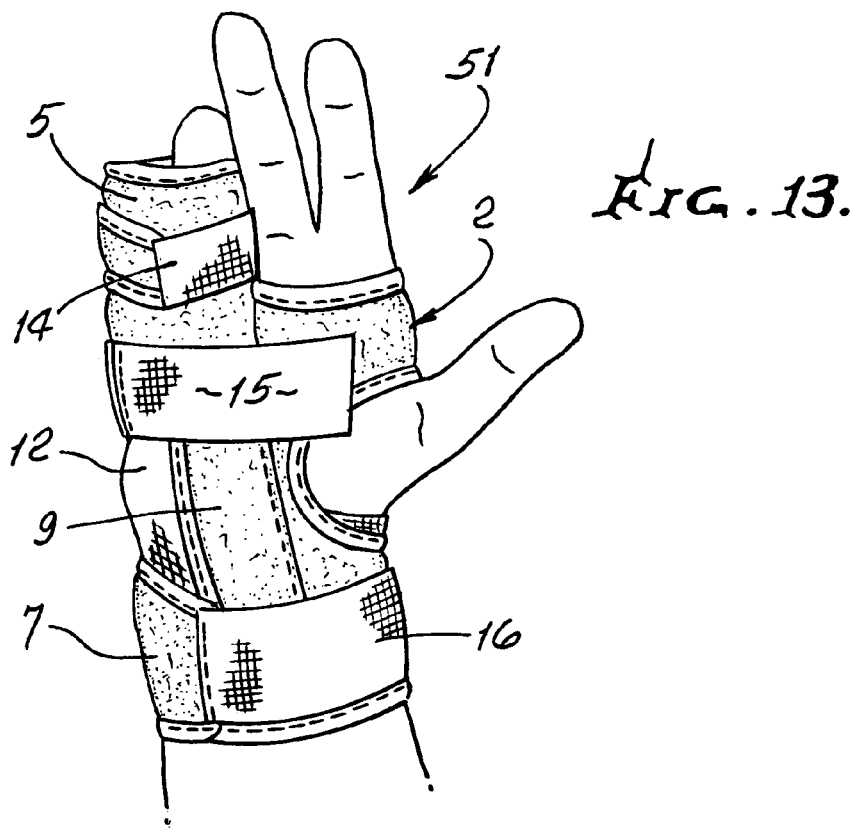
Figure 14:
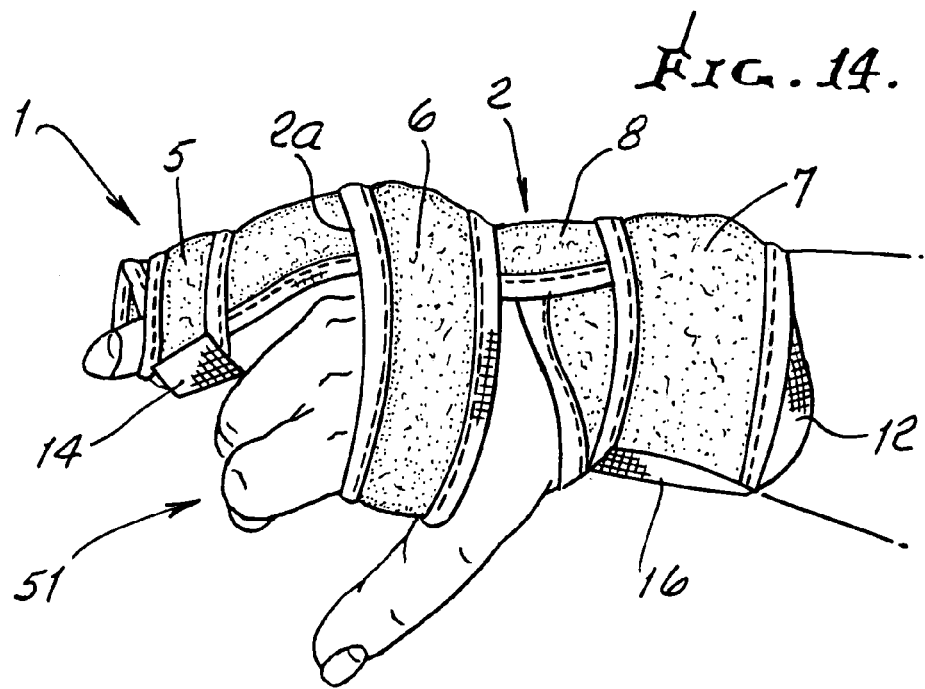

FIGS. 13 and 14 are views of the brace 1 applied to the right hand 51 that has undergone a boxer (metacarpal 4 and 5) fracture, that view otherwise referred to a "right lateral outside" view. Note the wrapped positions of the straps 5, 6 and 7 relative to the right hand.

FIGS. 15 and 16 are views of the brace 1, applied to the left hand 50 that has undergone a metacarpal 2 and 3 fracture, that view otherwise referred to as "left medial inside" view. Note the hand immobilizing positions of the three wrapped straps 5, 6 and 7 relative to the left hand structure as shown.

Although the present invention has been described in considerable detail with reference to certain preferred versions thereof, other versions are possible. Therefore, the spirit and scope of the invention should not be limited to the description of the preferred versions contained herein.

The invention further provides a multiple use reversible gauntlet brace, that can be used to immobilize metacarpal 4 and/or 5 and proximal phalange or phalanges 4 and/or 5 on the right hand, and metacarpal 2 and/or 3 and proximal phalange or phalanges 2 and 3 on the left hand. When turned over, the reversible brace can be used to immobilize metacarpal 4 and/or 5 and proximal phalange or phalanges 4 and 5 on the left hand, and metacarpal 2 and/or 3 and proximal phalange or phalanges 2 and/or 3 on the right hand. Malleable stays in or on the brace are typically bent or re-bent to conform to the selected use, prior to application of the brace to the hand and wrist.

When using the brace for $4^{th}$ and $5^{th}$ metacarpal fractures, the through opening 60 in body 2, between the stays, in lateral alignment with 6, as seen in FIG. 1, is not used. However, when the brace is used for the $2^{nd}$ and $3^{rd}$ metacarpal fractures, the thumb opening receives the user's thumb. See FIGS. 11, 12 and 18 for right hand, and see FIGS. 15 and 16 for left hand.

We claim:
1. In a finger and hand brace, the combination comprising:
 a) a longitudinally elongated brace body, adapted to be applied lengthwise to the wrist and finger regions of the hand, to exert compressive wrapping,
 b) multiple flexible flaps carried by the body to be spaced lengthwise thereof and to extend from the body, the flaps consisting of elastic material,
 c) the multiple separate flexible flaps configured to be securely wrapped about the hand, and at least one of the following:
  i) wrist
  ii) a finger or fingers,
 d) retention means on the brace to retain the flaps in wrapped condition,
 e) and two generally longitudinally elongated individually malleable stiffeners carried by said body, said stiffeners having lengthwise only undulating extent or extents, to readily conform to wrist, hand and finger contour with the fingers extended in natural condition, the stiffeners malleably bent to conform to selected use in conformance with retained flexed finger contours,
 f) said undulating extents of the stiffeners including:
  i) an upwardly facing convex curvature of one stiffener in unfolded condition of the brace, to conform to downwardly concave palm curvature after wrap-folding of the brace to bring the stiffener under the palm and fingers,
  ii) and a downwardly facing concave curvature of another stiffener to conform to upwardly convex knuckle contour in wrap-folded condition of the brace,
 g) said convex curvature positioned in juxtaposed facing relation to said concave curvature whereby the spacings between the stiffeners along their lengths are approximately the same,
 h) and including pockets in the body to receive the stiffeners, which are generally longitudinally extended, two of the flaps positioned to extend between the pockets and to be wrapped about both pockets, stiffeners therein, and body material associated therewith, to hold said undulating extents near the palm and knuckle, respectively in wrapped condition of the brace, and to exert compression on the pockets and stiffeners therein,
 i) the body having intermediate extent between the pockets and stiffeners and being folded to bring the two pocketed stiffeners and their curvatures into juxtaposed conformance as aforesaid, and to be wrapped by the flaps about said folded intermediate extent and about the pockets to exert positive retention compression on the pockets and stiffeners therein,
 j) the body having an extended position in substantially a flat plane, in which said intermediate extent is located between said pockets and defines a thumb or finger confining local region located between the two pockets, the body merging with said flaps at a side of one pocket opposite said intermediate extent, said intermediate extent extending lengthwise throughout the major length of the pockets,
 k) said multiple flaps defining straps including a first strap configured to secure one or more of the user's fingers, a second strap configured to secure the user's palm, and a third strap configured to secure the user's wrist, the second and third straps having about equal lengths which substantially exceeds the length of the first strap.

2. The finger and hand brace of claim 1 wherein said retention means includes locking devices associated with the straps, to lock the straps in position after being wrapped around certain of the patient's fingers, thereby to substantially immobilize the fingers relative to the hand.

3. The finger and hand brace of claim 1 wherein there is a cushioning structure associated with the pockets.

* * * * *